(12) United States Patent
Kono et al.

(10) Patent No.: US 6,268,541 B1
(45) Date of Patent: Jul. 31, 2001

(54) PROCESS FOR THE PREPARATION OF 1,1,1, 2,2-PENTAFLUOROETHANE

(75) Inventors: Satoru Kono; Takashi Shibanuma; Takashi Kanemura; Toshikazu Yoshimura; Kazuhiro Takahashi, all of Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/509,984
(22) PCT Filed: Oct. 6, 1998
(86) PCT No.: PCT/JP98/04500
  § 371 Date: Apr. 5, 2000
  § 102(e) Date: Apr. 5, 2000
(87) PCT Pub. No.: WO99/19285
  PCT Pub. Date: Apr. 22, 1999

(30) Foreign Application Priority Data

Oct. 9, 1997 (JP) .................................................. 9-276883

(51) Int. Cl.⁷ .................................................. C07C 17/08
(52) U.S. Cl. .................................................. 570/168; 570/169
(58) Field of Search ....................................... 570/168, 169

(56) References Cited

U.S. PATENT DOCUMENTS 5,623,092 * 4/1997 Scott et al. .......................... 570/168
5,763,707 * 6/1998 Scott et al. .......................... 570/168

FOREIGN PATENT DOCUMENTS 9-141105    6/1997  (JP) .
WO 96/13476 5/1996  (WO) .

* cited by examiner

*Primary Examiner*—Alan Siegel
(74) *Attorney, Agent, or Firm*—Larson & Taylor PLC

(57) ABSTRACT

The invention provides a process for the preparation of 1,1,1,2,2-pentafluoroethane by fluorinating in the gas phase a halogenated hydrocarbon feedstock containing 2-chloro-1,1,1,2-tetrafluoroethane with hydrogen fluoride, the process being characterized in that:

(i) a fluorinated chromium oxide obtained by fluorinating a chromium oxide represented by the formula: $CrO_m$ ($1.5 < m < 3$) is used as the catalyst,
(ii) the mixing ratio (by mole) of hydrogen fluoride to halogenated hydrocarbon feedstock ranges from 1.5 to 10, and
(iii) the fluorination is conducted at a temperature of 250 to 350° C. The process makes it possible to prepare easily HFC-125 reduced in the contents of CFCs.

5 Claims, No Drawings

PROCESS FOR THE PREPARATION OF 1,1,1, 2,2-PENTAFLUOROETHANE

This application is a 371 of PCT/JP98/04500 filed Oct. 6, 1998.

TECHNICAL FIELD

The present invention relates to a process for the preparation of 1,1,1,2,2-pentafluoroethane (HFC-125).

BACKGROUND ART 1,1,1,2,2-pentafluoroethane (HFC-125), which is a useful hydrofluorocarbon compound for its zero ozone depleting potential, is used in various applications such as foaming agent, propellant, refrigerant and the like.

Known processes for preparing HFC-125 include a process comprising fluorinating 2-chrolo-1,1,1,2-tetrafluoroethane (HCFC-124) with hydrogen fluoride (HF) in the gas phase. According to this process, in addition to the desired HFC-125, HC1 is produced as a by-product which reacts with HCFC-124 (reverse reaction) to produce 2,2-dichloro-1,1,1-trifluoroethan (HCFC-123). Further, the process produces impurities including chrolofluoroethanes (CFCs) such as 1,2,2-trichrolo-1,1,2-trifluoroethane (CFC-113), 2,2,2-trichrolo-1,1,1-trifluoroethane (CFC-113a), 1,2-dichrolo-1,1,2,2-tetrafluoroethane (CFC-114), 2,2-dichrolo-1,1,1,2-tetrafluoroethane (CFC-114a), 2-chrolo-1,1,1,2,2-pentafluoroethane (CFC-115), etc.; 2-chrolo-1,1,1-trifluoroethane (HCFC-133a), 1,1,1,2-tetrafluoroethane (HFC-134a) and the like.

The unreacted HCFC-124 and HCFC-123 formed in the reverse reaction can be converted into the desired HFC-125 by fluorination and, therefore, they can be recycled to the process and economically reused as starting materials. On the contrary, the CFCs, HCFC-133a and HFC-134a can not be fluorinated to form HFC-125 and, therefore, the ratios of these components in the reaction product need to be minimized to improve the yield of HFC-125. Especially, CFC-115 is difficult to be separated from HFC-125 because it has a boiling point close to that of HFC-125, which leads to a degraded purity of the desired HFC-125. Therefore, production of CFC-115 should be kept as low as possible. Further, CFC-113a and CFC114a have close boiling points to those of HCFC-123 and HCFC-124, which necessitates a fractionator having a large number of trays in order to separate them completely. If HCFC-123 and HCFC-124 are recycled to the process as starting materials without being purified by a fractionator, CFC-113a and CFC-114a are unavoidably contained in the starting materials. These CFCs are fluorinated in the process to eventually give CFC-115, thereby further degrading the purity of CFC-125.

As described above, the separation of CFC-115 from CFC-125 is difficult, and the separation necessitates additional apparatuses for extractive distillation and the like, which leads to increased costs of equipment and production. Besides, the ban on CFCs has been agreed by international conventions and, therefore, the production should be decreased. Thus, there is a demand for a process for the production of HFC-125 by fluorinating HCFC-124 wherein the formation of CFCs is suppressed as low as possible.

Among the known processes for the preparation of HFC-125 using HCFC-124 as a starting material with reduced production of CFCs, U.S. Pat. No. 5,475,167 discloses a process which uses as catalyst $Cr_2O_3$ having a high surface area or $Cr_2O_3$ pretreated with CO, $H_2$ or $H_2O$. However, the process requires maintaining the production ratio of HFC-125 at a level of 50% or higher. According to the Examples in this U.S. patent, it is necessary to conduct the reaction at a high temperature of 350° C. or higher with relatively long contact time of 6.8 (g·s/cc) for achieving the above production ratio. Further, it is observed from the Examples of the above patent that the production of CFCs is not suppressed satisfactorily. Specifically, though the production of CFCs is lowest in the case where a high surface area $Cr_2O_3$ catalyst is used, the production ratio of CFCs (ratio of CFCs relative to HFC-125 produced) therein is about 3000 ppm. In other cases, the production ratios are 5000 ppm or larger.

U.S. Pat. No. 5,334,787 discloses a process for preparing HFC-125 by reacting in the gas phase HCFC-123 or HCFC-124 used as a starting material with HF in the presence of a $Cr_2O_3$ catalyst. However, it is necessary also in this process to maintain the production ratio of HFC-125 at 50% or higher for inhibiting the production of CFCs, which results in the relatively long contact time of 10–100 seconds. The production of the CFCs is not satisfactorily suppressed also by the process.

Furthermore, U.S. Pat. No. 5,399,549 discloses a process for preparing HFC-125 by reacting in the gas phase HCFC-123 or HCFC-124 used as a starting material with HF in the presence of a $Cr_2O_3$ catalyst. However, also in this process, the production of CFCs is not satisfactorily suppressed.

DISCLOSURE OF INVENTION

A primary object of the present invention is to provide a process for the preparation of HFC-125 by fluorinating in the gas phase a halogenated hydrocarbon feedstock containing HCFC-124, wherein the production of CFCs is minimized.

In view of the deffects of the above known processes, the present inventors conducted an extensive research to produce HFC-125 with very low contents of CFCs by the fluorination of HCFC-124 containing feedstock with HF in the gas phase. As a result, the inventors found that when the fluorination is conducted in the presence of a fluorinated chromium oxide catalyst obtained by fluorinating chromium oxide represented by the formula: $CrO_m$ (1.5<m<3) with HF, in a specific range of mixing ratios of the halogenated hydrocarbon to HF and in a specific range of reaction temperatures, the desired HFC-125 with greatly reduced CFCs contents can be obtained. Moreover, the inventors found that the ratio of CFCs to HFC-125 can be reduced by decreasing the yield of the desired HFC-125, and that the HFC-125 with a remarkably reduced content of CFCs can be produced especially when maintaining the yield of HFC-125 at less than 50%. The invention was accomplished based on these new findings.

The present invention provides the following process for the production of HFC-125.

(1) A process for the preparation of 1,1,1,2,2-pentafluoroethane by fluorinating in the gas phase a halogenated hydrocarbon feedstock containing 2-chloro-1,1,1,2-tetrafluoroethane with hydrogen fluoride, the process being characterized in that:

(i) a fluorinated chromium oxide obtained by fluorinating a chromium oxide represented by the formula: $CrO_m$ (1.5<m<3) is used as a catalyst, (ii) the mixing ratio (by mole) of hydrogen fluoride to halogenated hydrocarbon feedstock ranges from 1.5 to 10, and (iii) the fluorination is conducted at a temperature of 250 to 350° C.

(2) A process according to item (1), wherein the halogenated hydrocarbon feedstock is 2-chloro-1,1,1, 2tetrafluoroethane or a mixture of 2-chloro-1,1,1,2-tetrafluoroethane and 2,2-dichloro-1,1,1-trifluoroethane containing at least 50 mole % of 2-chloro-1,1,1,2-tetrafluoroethane.

(3) A process according to the item (1) or (2), wherein the yield of 1,1,1,2,2-pentafluoroethane is controlled at a level lower than 50%.

(4) A process according to any one of the items (1) to (3), wherein the fluorinated chromium oxide has a specific surface area of 25–130 m$^2$/g.

(5) A process according to any one of the items (1) to (4), wherein 2-chloro-1,1,1,2-tetrafluoroethane, 2,2-dichloro-1,1,1-trifluoroethane and hydrogen fluoride in the reaction mixture are recycled to the process as feedstock.

In the invention, it is necessary to use, as a fluorination catalyst, a catalyst obtained by fluorinating with hydrogen fluoride (HF) a chromium oxide represented by the formula: CrOm (1.5<m<3). By using such a specific catalyst, the amount of CFCs contained in the reaction products can be reduced. The catalyst can be prepared by the process disclosed in Japanese Unexamined Patent Publication No. 146680/1993. The process for the preparation of the catalyst employed in the present invention is illustrated briefly in the following.

The chromium oxide is represented by the formula: CrOm, wherein m is in the range of 1.5<m<3, preferably 2<m<2.75, more preferably 2<m<2.3.

One of the examples for the preparation process of the chromium oxide is described below.

First, an aqueous solution of chromium salt (chromium nitrate, chromium chloride, chrome alum, chromium sulfate, etc.) is mixed with aqueous ammonia to obtain a precipitate of chromium hydroxide. For example, the precipitate of chromium hydroxide can be obtained by adding dropwise a 10% aqueous ammonia to a 5.7% chromium nitrate solution in an amount of 1 to 1.2 equivalent weight of ammonia per equivalent weight of chromium nitrate. The properties of the chromium hydroxide can be controlled by the reaction rate during the precipitation. A higher reaction rate is preferred. The reaction rate varies depending on the temperature of reaction solution, mixing procedure of aqueous ammonia (mixing rate), stirring condition and the like.

The precipitate is filtrated, washed and dried. The drying may be conducted, for example, by air-drying at a temperature of about 70–200° C., preferably about 120° C., for about 1–100 hour(s), preferably about 12 hours. The product at this stage is herein called a "state of chromium hydroxide". Next, the dried product is disintegrated into small particles. The rate of precipitation is preferably adjusted prior to this stage, so that the density of the disintegrated powder (for example, having a particle size of not more than 1000 μm, and 95% of powder having sizes between 46–1000 μm) is in the range of about 0.6–1.1 g/ml, preferably of about 0.6–1.0 g/ml. If the density of the powder is lower than 0.6 g/ml, the strength of pellets will be undesirably low. On the other hand, if the density of the powder is higher than 1.1 g/ml, catalyst activity will be low and the pellets are prone to crack. The specific surface area of the powder may preferably be about 100 m$^2$/g or larger, more preferably about 120 m$^2$/g or larger, after degassing at 200° C. for 80 minutes. The upper limit of the specific surface area is, for example, about 220 m$^2$/g.

Then, the chromium hydroxide powder is formed into pellets by means of a compacting machine. The chromium hydroxide power may be mixed with graphite, when so required, in an amount of about 3 wt. % or less prior to the pellet formation. The pellet size may be about 3.0 mm in diameter and about 3.0 mm in height, for example. The pellets may preferably have a compressive strength (pellet strength) of about 210±40 kg/cm$^2$. In the case where the compressive strength is too high, the gas contact efficiency declines to lower the catalyst activity and the pellets become cracky. On the other hand, pellets with a low compressive strength are liable to be powdered, which results in handling difficulty.

Formed pellets are fired in an inert atmosphere, for example, in a nitrogen gas stream to give an amorphous chromium oxide. The firing temperature may preferably be not lower than 360° C. However, since chromium oxide is crystallized at exceedingly high temperatures, it is desirable that the firing temperature is maintained at the highest within the range of temperatures where the crystallization of chromium oxide is avoidable. Specifically, the pellets may be fired at a temperature of about 380–460° C., especially about 400° C., for about 1–5 hours, especially about 2 hours.

The fired chromium oxide may have a specific surface area of about 170 m$^2$/g or larger, preferably about 180 m$^2$/g or larger, more preferably about 200 m$^2$/g or larger. There is no upper limit for the specific surface area. The specific surface area smaller than 170 m$^2$/g is undesirable since it diminishes the catalyst activity.

The chromium oxide is then fluorinated with hydrogen fluoride (HF treatment). The fluorination temperature may suitably be maintained within the temperature range where the water formed does not condense (for example, about 150° C. at 1 atmospheric pressure), and the upper limit may be at a temperature where the catalyst does not crystallize by the heat of reaction. The pressure during fluorination is not critical, but the fluorination may preferably be conducted at the same pressure as that in the catalytic reaction. The fluorination temperature is, for example, in the range of about 100–460° C.

The surface area of the catalyst is diminished by the fluorination. The catalyst usually shows a higher activity when the specific surface area is greater. The specific surface area of the catalyst after the fluorination may preferably be about 25–130 m$^2$/g, more preferably about 40–100 m$^2$/g, but it is not limited to the above range.

The process for the preparation of HFC-125 according to the invention comprises fluorinating in the gas phase a halogenated hydrocarbon feedstock with hydrogen fluoride (HF) in the presence of the above-described fluorinated chromium oxide as a catalyst.

It is necessary to use, as the starting material, halogenated hydrocarbon feedstock containing at least HCFC-124. As a result of the fluorination of the halogenated hydrocarbon feedstock containing HCFC-124, HFC-125 is produced as a reaction product, while a portion of unreacted HCFC-124 reacts with by-product HCl to produce HCFC-123. The remaining portion of unreacted HCFC-124 and the produced HCFC-123 can be recycled to the process as starting materials together with unreacted HF since both of them can be converted into the desired HFC-125 by fluorination. Because these components are extremely high in the boiling points compared with the desired HFC-125, they can easily be separated from HFC-125 by condensing only the fraction containing HCFC-123, HCFC-124 and HF by means of a heat exchanger or the like. In the case where the components are recycled to the process as starting materials, the halogenated hydrocarbon feedstock for fluorination is a mixture of HCF-123 and HCFC-124. HCFC-123 may be newly fed in addition to recycled portion contained in the reaction mixture.

When using the mixture of HCFC-123 and HCFC-124 as a feedstock, the mixture preferably contains HCFC-124 in an amount not less than 50 mole %, more preferably not less than 80 mole % of the total amount of the mixture. Production ratio of CFCs is decreased as the proportion of HCFC-124 in the starting material increases.

The proportion of gaseous hydrogen fluoride (HF) used for fluorination to HCFC-124 or to the mixture of HCFC-123 and HCFC-124 as the halogenated hydrocarbon feedstock is preferably about 1.5–10, more preferably about 2–4 in terms of the mixing ratio (by mole) of HF/halogenated hydrocarbon feedstock at the inlet of the reactor. The production of CFCs can be suppressed by increasing the mole ratio of HF; however, it is undesirable from the economic point of view to use an excessive amount of HF. Therefore, the amount of HF to be used may suitably be selected within the range of the above mixing ratio.

Type of the reactor to be employed for the fluorination is not critical, and a tubular reactor, fluidized bed column or the like may be used.

The fluorination reaction temperature may be in the range of about 250–350° C., preferably about 280–320° C. The yield of HFC-125 varies depending on the reaction temperature, and the yield is usually reduced as the fluorination reaction temperature is lowered provided that other conditions remain unchanged.

The reaction pressure is not critical, and the fluorination can be conducted at the atmospheric pressure or an increased pressure. Typically, the reaction pressure may preferably be about 0–10 kg/cm$^2$, more preferably about 0.5–4 kg/cm$^2$. In the case where the separation of HFC-125 from the reaction mixture is conducted under a pressure not lower than the atmospheric pressure, the fluorination is usually conducted under a increased pressure, but the reaction pressure is not limited by the separation pressure.

The contact time in the reactor is not limited, but may preferably be, as expressed as catalyst weight/volumetric feed rate of feedstock (HCFC-123, HCFC-124 and HF), about 1–20 g·s/cc, more preferably about 1–5 g·s/cc.

According to the invention, HFC-125 significantly reduced in the content of CFCs can be produced by conducting a fluorination under the above described conditions, i.e., using the specified fluorinated chromium oxide catalyst with the mixing ratio (by mole) of HF to halogenated hydrocarbon feedstock being 1.5–10 at the fluorination reaction temperature of 250–350° C.

In the fluorination reaction of the halogenated hydrocarbon feedstock according to the invention, the proportion of CFCs relative to HFC-125 tends to decline as the yield of the desired HFC-125 is diminished. Specifically, if the yield of HFC-125 is controlled at a level less than 50%, the production ratio of CFCs relative to HFC-125 typically becomes 0.4% or less, whereby enabling to obtain HFC-125 which is remarkably reduced in the content of CFCs.

According to the present invention, the yield of HFC-125 can be reduced usually by lowering the reaction temperature, shortening the reaction time and increasing the amount of HF feed. Thus, it is possible to control the yield of HFC-125 easily at a level less than 50% by suitably adjusting these parameters.

According to the invention, HFC-125 which is reduced in the content of CFCs can be produced easily.

BEST MODE FOR CARRYING OUT THE INVENTION

The invention will hereinafter be described in more detail with reference to Examples.

PREPARATION EXAMPLE 1

A catalyst for fluorination reaction was prepared in the following manner.

To 765 g of a 5.7% aqueous chromium nitrate solution was added 114 g of a 10% aqueous ammonia, and a precipitation obtained thereby was filtrated, washed and dried in air at a temperature of 120° C. for 12 hours to give chromium hydroxide. The chromium hydroxide was formed into pellets each having a diameter of 3.0 mm and a height of 3.0 mm, and then fired in a nitrogen gas stream for 2 hours. The obtained chromium oxide is identified as $CrO_{2.0}$ based on results of a quantitative analysis of the amount of Cr and an elemental analysis. A magnetic susceptibility measurement of the chromium oxide revealed that the number of the effective Bohr magnetrons expressed in the following equation was 2.64, which was close to the theoretical value of the number of the effective Bohr magnetrons of $Cro_{2.0}$ of 2.83. The theoretical value of the number of effective Bohr magnetrons of $Cr_2O_3$ is 3.87.

Number of Effective Bohr Magnetron(s)=(Susceptibility×temperature/0.125)$^{1/2}$ Next, a reaction tube made of Hastelloy C having an inner diameter of 15 mm was charged with 18.5 g of the above chromium oxide. While feeding HF to the reaction tube under the conditions of a feed rate of 10 cc/min and a contact time of 6.8 g·s/cc, fluorination of chromium oxide was conducted at a temperature of 200° C. for about 2 hours. As a result of the fluorination, the chromium oxide was converted to CrOxFy (2X+Y≈4, F concentration is about 18%) having a specific surface area of about 95 m$^2$/g.

EXAMPLES 1–4

After preparing the fluorinated chromium oxide catalyst in the manner described in Preparation Example 1, HCFC-124 at a feed rate of 55 cc/min and HF at a feed rate of 110 cc/min were fed to the reaction tube employed in the fluorination of the catalyst so as to fluorinate HCFC-124 at reaction temperatures shown in Table 1 below. Mole ratio of HF/HCFC-124 was 2, and the contact time was 6.8 g·s/cc (weight of catalyst/volumetric feed rates of HCFC-124 and HF).

The reaction mixture was then washed with water, and then analyzed by gas chromatography (trade name of the device used: Polapack N). Results of analyses of the reaction mixtures and the production ratios (selectivity) of CFCs relative to HFC-125 are shown in Table 1 below.

TABLE 1

| Ex. No. | Reaction Tempera- ture(° C.) | Reaction Mixture (mol %) | | | | | Selecti- vity of CFCs(%) |
|---|---|---|---|---|---|---|---|
| | | HCFC -123 | HCFC -124 | HFC- 125 | CFCs | CFC- 115 | |
| 1 | 280 | 3.2 | 75 | 21.7 | 0.02 | 0.0007 | 0.09 |
| 2 | 290 | 6.7 | 58.8 | 34.5 | 0.03 | 0.004 | 0.09 |
| 3 | 300 | 10.5 | 40.6 | 48.7 | 0.07 | 0.019 | 0.15 |
| 4 | 315 | 12.8 | 19.9 | 66.4 | 0.25 | 0.11 | 0.37 |

The above results reveal that HCF-125 with a reduced content of CFCs can be obtained by the process of the present invention. Further, it is evident that the lower the reaction temperature and the yield of HFC-125, the lower is the production ratio of CFCs. Specifically, when the yield of HFC-125 is lower than 50%, the production ratio of CFCs is significantly lowered.

EXAMPLE 5

Except for using 3.96 g of the catalyst and increasing the reaction temperature to 315° C., fluorination of HCFC-124 was conducted following the procedure in Example 1. However, the apparent volume of the effective reaction volume in the tube was changed to 3.2 cc with the change in the charged amount of catalyst and the contact time was about 1.2 seconds. The results of analysis for the reaction mixture and the production ratio (selectivity) of CFCs relative to HFC-125 are shown in Table 2 below.

TABLE 2

| Ex. No. | Reaction Temperature (° C.) | Reaction Mixture (mol %) | | | | Selectivity of CFCs (%) |
|---|---|---|---|---|---|---|
| | | HCFC-123 | HCFC-124 | HFC-125 | CFCs | |
| 5 | 315 | 7.0 | 50.6 | 42.3 | 0.039 | 0.09 |

EXAMPLE 6

Except for using, in place of HCFC-124, a mixture of HCFC-123/HCFC-124=17.3/82.7 fed at a feed rate of 55 cc/min and increasing the reaction temperature to 300° C., fluorination of HCFC-123 and HCFC-124 was conducted following the procedure in Example 1. The results of analysis for the reaction mixture and the production ratio (selectivity) of CFCs relative to HFC-125 are shown in Table 3 below.

TABLE 3

| Ex. No. | Reaction Temperature (° C.) | Reaction Mixture (mol %) | | | | Selectivity of CFCs (%) |
|---|---|---|---|---|---|---|
| | | HCFC-123 | HCFC-124 | HFC-125 | CFCs | |
| 6 | 300 | 17.3 | 40.1 | 42.2 | 0.17 | 0.4 |

EXAMPLE 7

Except for using 5.9 g of the catalyst, changing the feed rates of HCFC-124 and HF respectively to 18.3 cc/min and 147 cc/min (HF/HCFC-124=8), and increasing the reaction temperature to 310° C., fluorination of HCFC-124 was conducted following the procedure in Example 1. The results of analysis for the reaction mixture and the production ratio (selectivity) of CFCs relative to HFC-125 are shown in Table 4.

TABLE 4

| Ex. No. | Reaction Temperature (° C.) | Reaction Mixture (mol %) | | | | Selectivity of CFCs (%) |
|---|---|---|---|---|---|---|
| | | HCFC-123 | HCFC-124 | HFC-125 | CFCs | |
| 7 | 310 | 2.0 | 66.3 | 31.6 | 0.017 | 0.055 |

What is claimed is:

1. A process for the preparation of 1,1,1,2,2-pentafluoroethane comprising fluorinating in the gas phase a hydrogenated hydrocarbon feedstock containing 2-chloro-1,1,1,2-tetrafluoroethane with hydrogen fluoride, the process being characterized in that:

(i) a fluorinated chromium oxide obtained by fluorinating a chromium oxide represented by the formula: $CrO_m$ ($1.5<m<3$) is used as a catalyst, (ii) the mixing ratio (by mole) of hydrogen fluoride to halogenated hydrocarbon feedstock ranges from 1.5 to 10, and (iii) the fluorination is conducted at a temperature of 250 to 350° C.

2. A process according to claim 1, wherein the halogenated hydrocarbon feedstock is 2-chloro-1,1,1,2-tetrafluoroethane or a mixture of 2-chloro-1,1,1,2-tetrafluoroethane and 2,2-dichloro-1,1,1-trifluoroethane containing at least 50 mole % of 2-chloro-1,1,1,2-tetrafluoroethane.

3. A process according to claim 1, wherein the yield of 1,1,1,2,2-pentafluoroethane is less than 50%.

4. A process according to claim 1, wherein the fluorinated chromium oxide has a specific surface area of 25–130 $m^2/g$.

5. A process according to claim 1, wherein 2-chloro-1,1,1,2-tetrafluoroethane, 2,2-dichloro-1,1,1-trifluoroethane and hydrogen fluoride are recycled to the process as the feedstock.

* * * * *